United States Patent [19]

Schmieding

[11] Patent Number: 5,423,823
[45] Date of Patent: Jun. 13, 1995

[54] CORING REAMER

[75] Inventor: Reinhold Schmieding, Naples, Fla.

[73] Assignee: Arthrex Inc., Naples, Fla.

[21] Appl. No.: 19,356

[22] Filed: Feb. 18, 1993

[51] Int. Cl.⁶ ............................................. A61B 17/16
[52] U.S. Cl. ..................................... 606/80; 606/179; 606/180
[58] Field of Search ............... 606/80, 79, 96, 87, 606/88, 102, 179, 180, 172; 128/898, 754; 408/204, 203.5, 207–209, 703, 68

[56] References Cited

U.S. PATENT DOCUMENTS

| | | | |
|---|---|---|---|
| 493,730 | 3/1893 | MacKenzie | 606/179 |
| 1,911,873 | 5/1933 | Balton | 408/68 |
| 2,573,462 | 10/1951 | Lindsey | 408/68 |
| 2,591,516 | 4/1952 | Darnell | 408/68 |
| 4,007,732 | 2/1977 | Kvavle et al. | 128/754 |
| 4,059,115 | 11/1977 | Jumashev et al. | 606/172 |
| 4,177,797 | 12/1979 | Baylis et al. | |
| 4,649,918 | 3/1987 | Pegg et al. | 128/754 |
| 4,741,651 | 5/1988 | Despres | 408/204 |
| 4,782,833 | 11/1988 | Einhorn et al. | |
| 4,913,143 | 4/1990 | Oloff et al. | 606/170 |
| 4,936,313 | 6/1990 | Burkhardt et al. | 128/751 |
| 5,197,967 | 3/1993 | Wilson | 606/79 |
| 5,211,647 | 5/1993 | Schmieding | 606/96 |
| 5,269,786 | 12/1993 | Morgan | 606/96 |

*Primary Examiner*—Tamara L. Graysay
*Attorney, Agent, or Firm*—Ostrolenk, Faber, Gerb & Soffen

[57] ABSTRACT

A coring reamer and method for creating a tibial tunnel and producing a bone graft for arthroscopic anterior cruciate ligament reconstruction. A conventional guide pin is drilled through the tibia and removed. A collared guide pin is then inserted through the guide pin tunnel until the collar abuts against the tibia. A cannulated core saw is slid over the guide pin and collar to engage the tibia. The tibial tunnel is reamed by driving the core saw into the tibia.

10 Claims, 5 Drawing Sheets

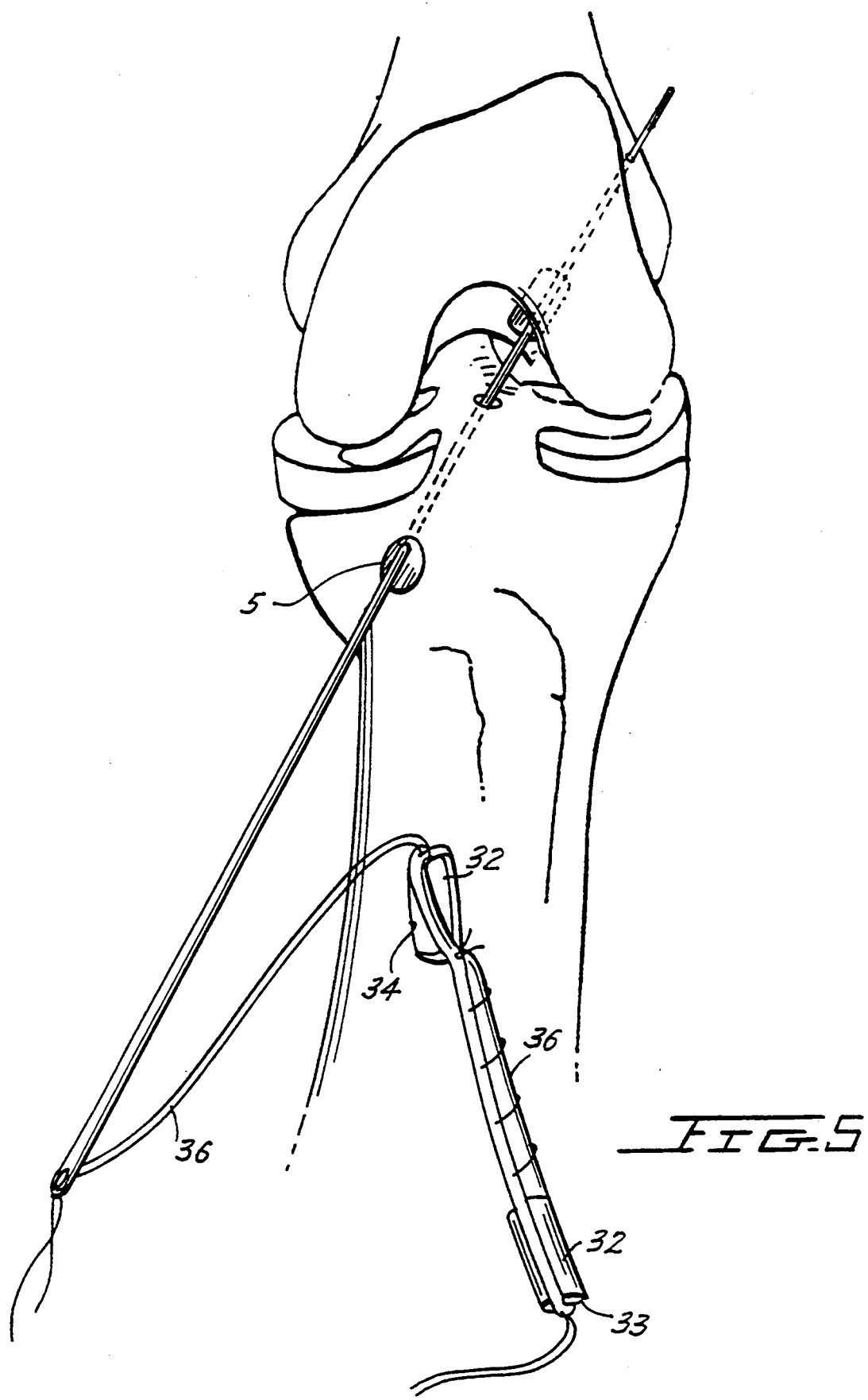

CORING REAMER

BACKGROUND OF THE INVENTION

1. Field of the Invention

The present invention relates to a coring reamer for creating a tibial tunnel and for producing a cancellous bone graft which can be used to fill a patella tendon graft harvesting site at the tibial tubercle and patella of the knee and as a hamstring tendon ACL graft fixation.

2. Description of the Prior Art

When a ligament or tendon becomes detached from the bone, surgery is usually required to re-secure the ligament or tendon. Often, a substitute ligament or graft is attached to the bone to facilitate regrowth and permanent attachment. The reattachment procedure involves drilling of a graft tunnel between two bones, for example, the tibia and the femur.

To achieve optimal results, it is important that the graft tunnel be drilled at a particular angle and location through the tibia and femur. This can be accomplished by using a variety of tools, such as sighting devices or marking hooks. See U.S. Pat. Nos. 5,269,786 and 5,320,626, assigned to the same assignee as the present application, for examples of such devices.

Surgical devices for coring bone, commonly known as trephine cutters, are disclosed in U.S. Pat. Nos. 4,782,833 and 4,913,143. Such devices do not include means for conveniently removing the cut-out bone from the instrument, are not guided over a guide pin, and are not intended for use in arthroscopic surgery.

SUMMARY OF THE INVENTION

It is an object of the present invention to provide a coring reamer which accurately produces a tibial tunnel and simultaneously creates a bone graft for later use in anterior cruciate ligament reconstruction.

The present invention provides a coring reamer for creating a tibial tunnel and for simultaneously producing a bone graft for arthroscopic anterior cruciate ligament reconstruction. The coring reamer of the invention includes an elongated collared guide pin which is inserted through a guide pin tunnel in the tibia. A cannulated core saw is inserted over the collared guide pin for drilling the tibia tunnel. A collar is spaced a predetermined distance from one end of the guide pin. As the core saw advances over the collared guide pin in drilling the tunnel, the bone mass generated by the drilling procedure fills the core of the reamer and pushes the collar back into the core. Upon completion of drilling, the pin, the saw, and the contained bone mass are removed from the patient's body. The core of bone mass is then removed from the core saw by tapping the end of the collared guide furthest from the collar. The core of bone mass can then be cut in half and used as bone blocks for subsequent hamstring graft fixation or filling of a harvested graft site.

Other features and advantages of the present invention will become apparent from the following description of the invention which refers to the accompanying drawings.

BRIEF DESCRIPTION OF THE DRAWINGS

FIG. 4A shows the initial position of the collar of the pin and the core saw prior to drilling. FIG. 4B shows the position of the collared pin within the core saw after drilling has begun. FIG. 4C illustrates the relationship between the collared pin, bone graft and the core saw.

FIG. 5 is a perspective view of the bone halves and tendon graft being inserted into the drilled tibial tunnel;

DETAILED DESCRIPTION OF THE PREFERRED EMBODIMENT

Figure 1:
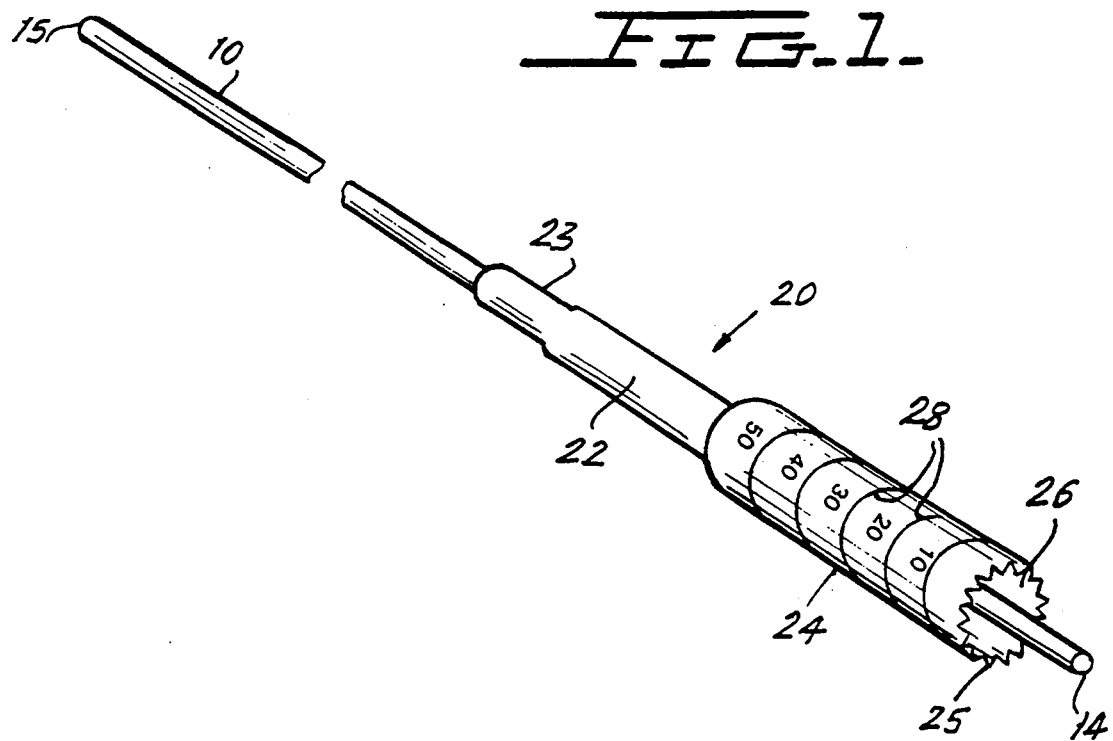
FIG. 1 is a perspective view of the coring reamer of the present invention.

Referring to FIG. 1, the present device is a core reamer for creating a tibial tunnel and producing a bone graft for use in anterior cruciate ligament (ACL) reconstruction.

Figure 2:
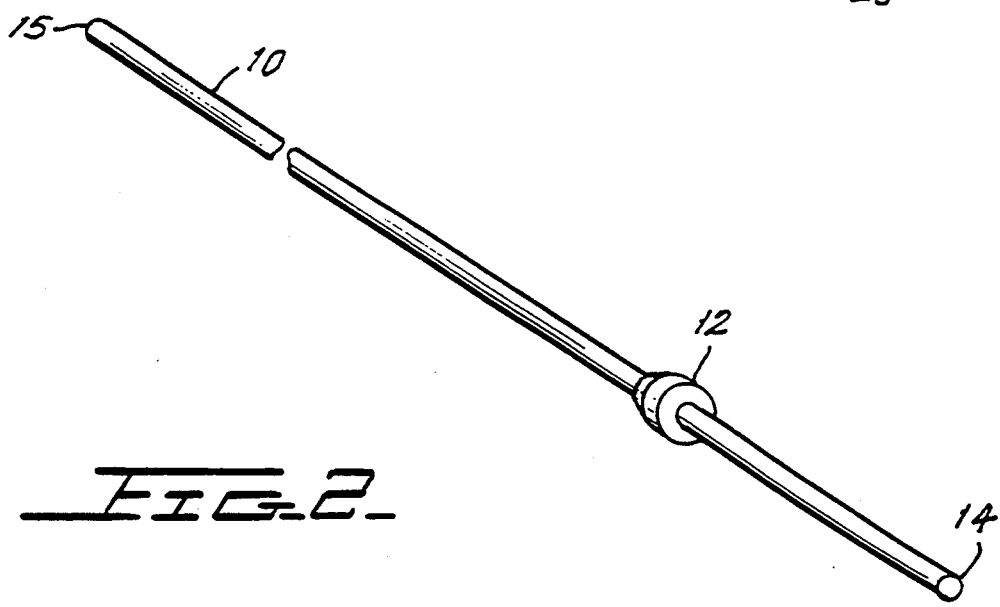
FIG. 2 is a perspective view of the collared pin of the present invention.

The device comprises an elongated guide pin 10 having opposed ends 14, 15. As shown in FIG. 2, a collar 12 is located on the pin, spaced from end 14. The collar has a diameter greater than the diameter of the guide pin, preferably approximately 0.35 inches(8.89 mm), whereas the diameter of pin 10 is approximately 0.09 inches (2.29 mm). Collar 12 is preferably spaced about 2 inches (50.8 mm) from end 14, with the overall length of the collared guide pin being approximately 15 inches (381 mm).

A cannulated core saw 20 is inserted over collared guide pin 10 from the end 15. The saw includes a hollow shaft 22 which has longitudinal depressions 23 spaced around its circumference for engagement with a drill chuck (not shown). The inner diameter of shaft 22 is slightly larger than the diameter of collared guide pin 10 to allow the passage of guide pin therethrough. Shaft 22 includes a proximal end and a distal end.

Connected to the distal end of shaft 22 is the core 24. Core 24 includes an open end 26 having a plurality of offset teeth 25, preferably, twenty-four teeth per inch. Circumferential markings 28 are provided at spaced intervals along the outside surface of core 24 to aid the surgeon in gauging the depth of the tibial tunnel.

Figure 3:
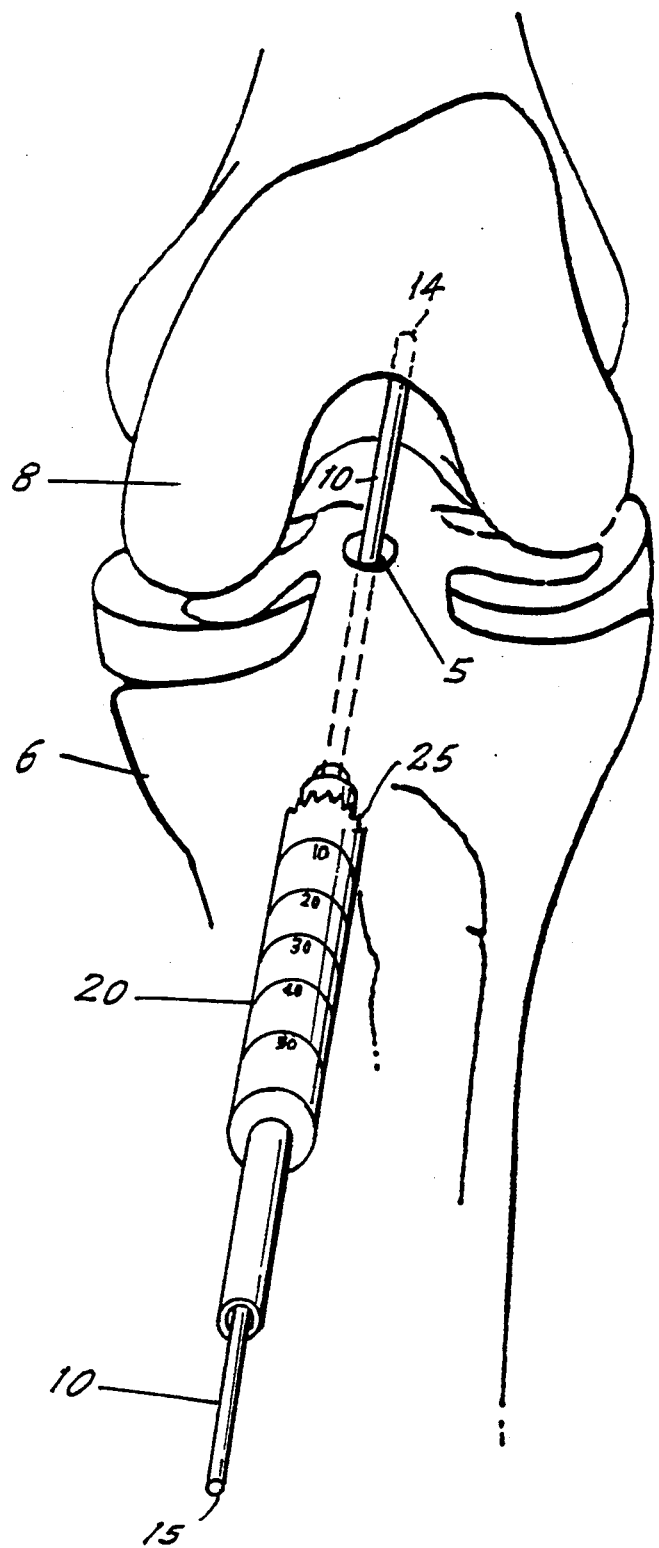
FIG. 3 is a perspective view of the coring reamer at the location of the tibial tunnel prior to drilling.

Referring to FIG. 3, prior to the insertion of collared guide pin 10 into the tibia 6 and patella 8, a guide tunnel 5 is drilled using a standard 2.4 mm guide pin (not shown). A tibial guide such as disclosed in U.S. Pat. Nos. 5,269,786 and 5,320,626 can be used to properly orientate the position of guide tunnel 5. The collared end 14 of guide pin 10 is then placed in the guide tunnel. When the end 14 of the pin 10 is inserted into tunnel 5, the collar 12 abuts against the tibia. The diameter of the collar is larger than the diameter of guide tunnel 5. The core saw 20 is inserted over the guide pin and collar 12 so that the teeth 25 abut against the tibia. Using collared pin 10 as a guide, the core saw is driven to bore a tibial tunnel into the tibia. During drilling, collar 12 advantageously acts as a centering guide to prevent sideways deflection of the coring reamer.

Figure 4A:
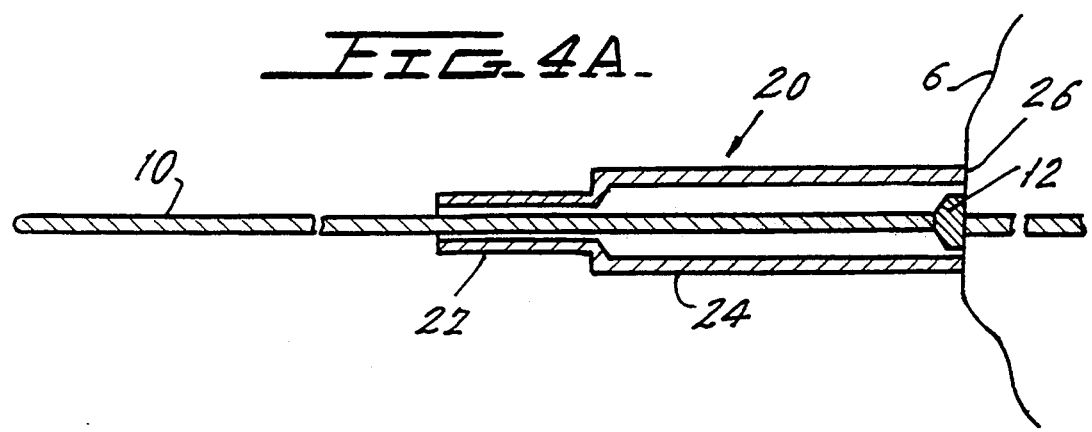
FIG. 4A–4C are cross-sectional side views of the assembled core saw and collared pin.
Figure 4B:
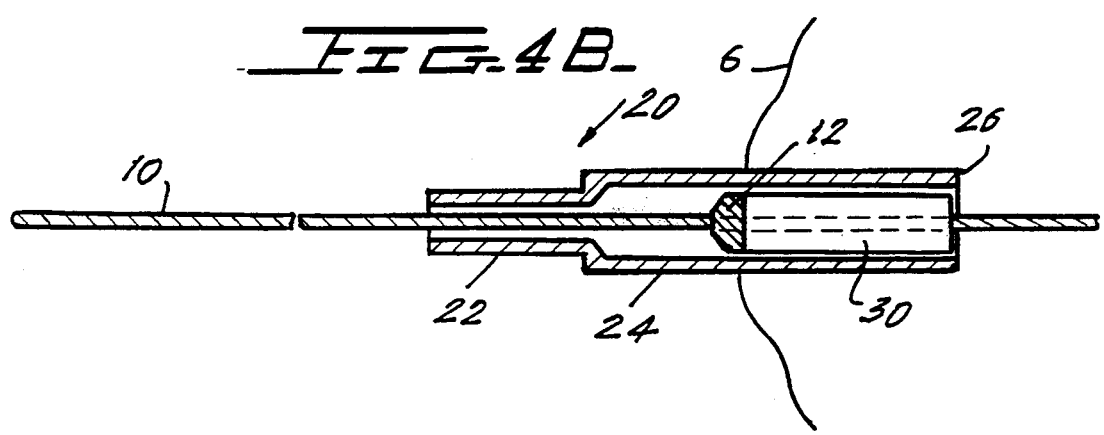
Figure 4C:
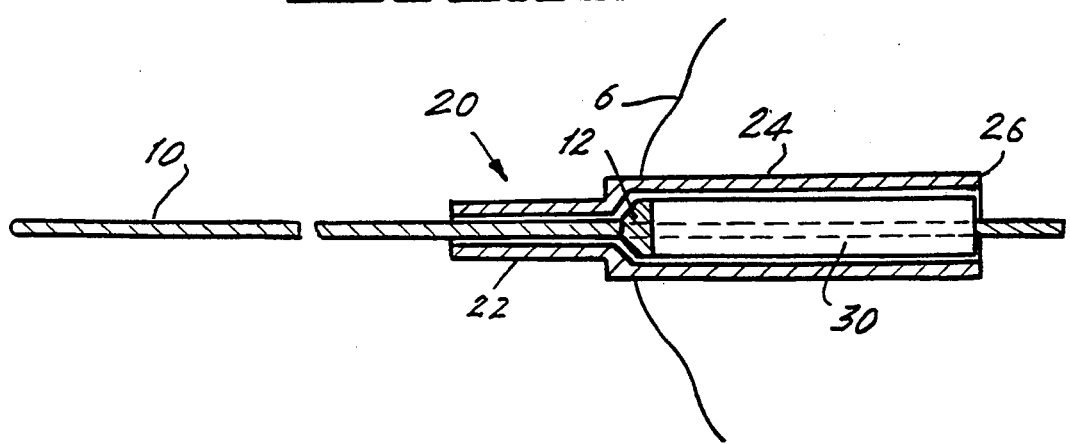

As shown in FIG. 4A, prior to drilling, the collar 12 is aligned with open end 26 of core 24. As drilling progresses, core 24 is driven into the tibia and the drilled bone mass 30, which rests on collar 12, enters and fills the interior of core 24. See FIG. 4B. Depending upon the length of the tunnel to be drilled, the entire core 24 may be filled with bone mass 30 upon completion of drilling. As shown in FIG. 4C, collar 12 acts as a stop for preventing core saw 20 from being driven further into the tibia once the collar reaches the end of the core 24. Throughout the entire drilling procedure, the guide pin extends through the center of bone mass 30. As the saw is driven into the tibia, the bone mass 30 pushes against collar 12 to automatically push guide pin 12 outward.

Upon completion of drilling, collared pin 10, saw 20 and bone mass 30 are removed from the knee. The core of bone mass 30 is removed from core saw 20 by tapping end 15 of guide pin with a hammer. The chuck of the drill used to drive saw 20 is tightened as far up as possible on cannulated shaft 22, so that pin end 15 protrudes out of the proximal end of the shaft 22 and the back of the drill. This allows the pin end to be tapped with the hammer while holding the saw with the drill to improve stability.

Figure 6:
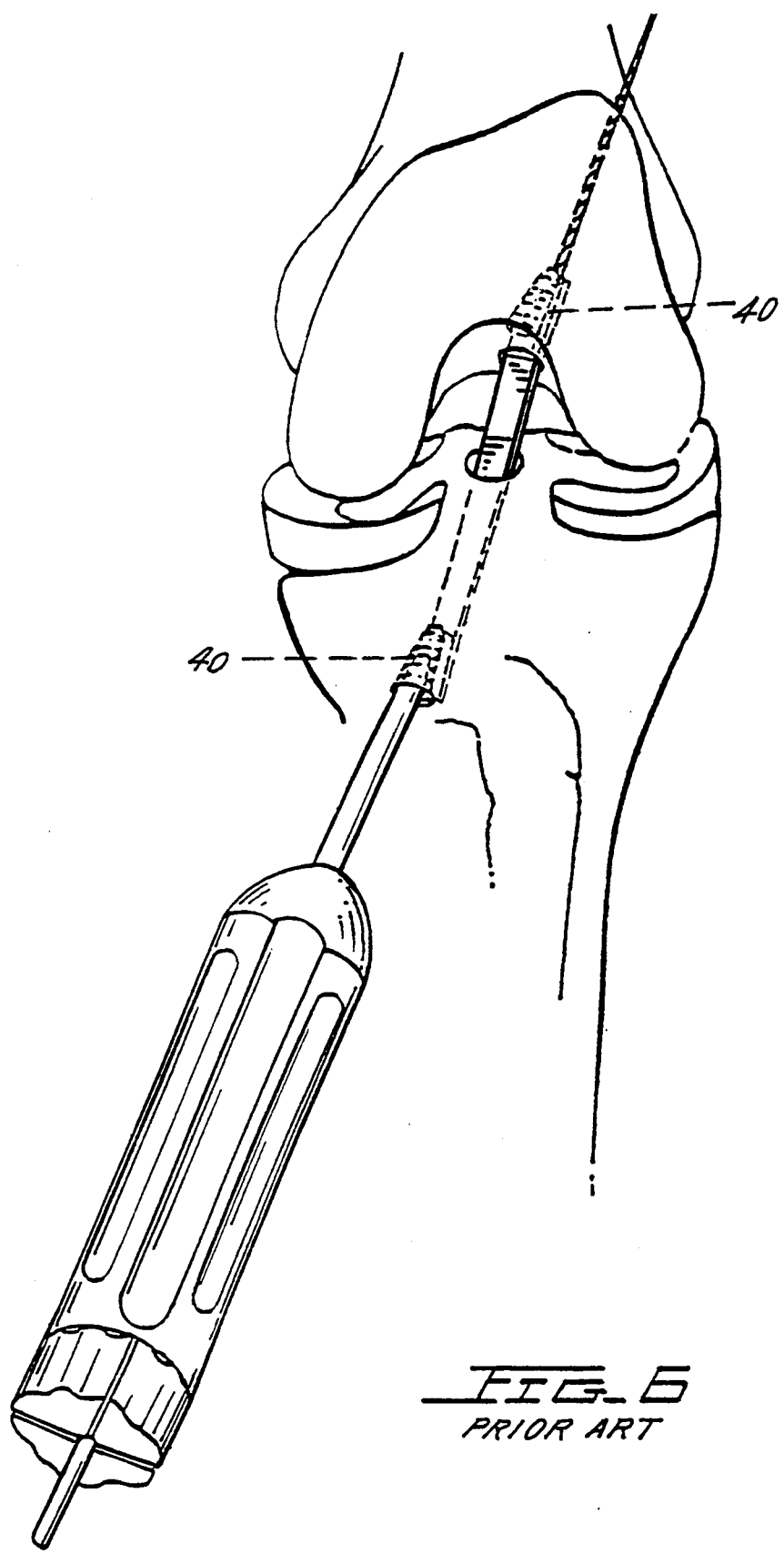
FIG. 6 represents the prior art and illustrates interference screws driven between the bone masses and the corresponding bone blocks.

For further surgical procedures, shown in FIG. 5, the core of bone mass 30 is saved and sawed into two separate halves 32. A bone core driving pin (not shown) is introduced into the center hole of one of the halves. This half is put in a shaping block and a small diameter burr is used to groove the side and top 33 of the bone core for accommodating the wrapping of a tendon 34 over the bone core. The tendon and bone core are fixed together by sutures and pulled through the tibial tunnel produced by the coring reamer of the present invention. The tendon and bone core are fixated within the tibial tunnel by an interference screw 40, as shown in FIG. 6. See e.g., U.S. Pat. Nos. 4,927,421 and 4,950,270. See also Applicant's U.S. Pat. No. 5,211,647.

The other half of the bone core is placed onto the driving pin and driven into the tibial tunnel between the exiting tendon ends which are held under tension in zero degrees of knee flexion. The tendon is tied over the bone core and secured with a suture. This bone core is also fixated with an interference screw as shown in FIG. 6.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for creating a tibial tunnel and producing a bone graft for arthroscopic anterior cruciate ligament reconstruction, comprising the steps of:
    drilling a guide tunnel through the tibia;
    inserting a guide pin through the guide tunnel, said guide pin having opposed ends and a collar spaced from one of the ends, until the collar abuts against the tibia;
    sliding a cannulated core saw over said guide pin and collar to engage the tibia; and
    reaming the tibial tunnel by driving the core saw into the tibia.

2. The method of claim 1, wherein, in the step of reaming the tibial tunnel, bone material collects within the core saw, said bone material resting against the collar of the guide pin.

3. The method of claim 2, further comprising the steps of removing the guide pin and core saw from the reamed tibial tunnel and subsequently removing the bone material from the core saw by pushing the collared end of the guide pin from the core saw.

4. The method of claim 7, further comprising the step of saving the bone material removed from the core saw and sawing the bone material into two separate halves.

5. The method of claim 4, further comprising the step of burring a groove on a side and top of one of the bone material halves for accommodating the wrapping of a tendon over the bone material.

6. The method of claim 5, further comprising the steps of fixing the tendon to the bone material half with sutures, pulling the bone material half and tendon through the tibial tunnel produced by the core saw, and fixing the bone material half within the tibial tunnel.

7. The method of claim 1, wherein an interference screw is used to fix the bone material half within the tibial tunnel.

8. The method of claim 4, further comprising the steps of fixing the tendon to the bone material half, pulling the bone material half and tendon through the tibial tunnel produced by the core saw, and fixing the bone material half within the tibial tunnel.

9. The method of claim 8, wherein an interference screw is used to fix the bone material half within the tibial tunnel.

10. The method of claim 3, further comprising the steps of saving the bone material removed from the core saw, fixing a tendon to the bone material, pulling the bone material and tendon through the tibial tunnel produced by the core saw, and fixing the bone material within the tibial tunnel.

* * * * *